United States Patent
Xu et al.

(10) Patent No.: US 10,444,074 B1
(45) Date of Patent: Oct. 15, 2019

(54) SPECTRUM RECOVERY IN A SAMPLE

(71) Applicant: Datacolor Inc., Lawrenceville, NJ (US)

(72) Inventors: Zhiling Xu, West Windsor, NJ (US);
Hong Wei, Princeton, NJ (US);
Taeyoung Park, Princeton Junction, NJ (US)

(73) Assignee: DATACOLOR INC., Lawrenceville, NJ (US)

( * ) Notice: Subject to any disclaimer, the term of this patent is extended or adjusted under 35 U.S.C. 154(b) by 0 days.

(21) Appl. No.: 15/939,044

(22) Filed: Mar. 28, 2018

(51) Int. Cl.
*G01J 3/46* (2006.01)
*G01N 21/25* (2006.01)
*G06F 17/16* (2006.01)

(52) U.S. Cl.
CPC ............ *G01J 3/462* (2013.01); *G01N 21/255* (2013.01); *G06F 17/16* (2013.01); *G01J 2003/467* (2013.01)

(58) Field of Classification Search
CPC .................................................. G01J 3/46–465
See application file for complete search history.

(56) References Cited

U.S. PATENT DOCUMENTS

| 8,532,371 | B2 | 9/2013 | Agarwal et al. | |
| 9,952,102 | B1* | 4/2018 | Xu | G01J 3/465 |
| 2008/0088557 | A1* | 4/2008 | Choi | G09G 3/3413 345/88 |
| 2008/0100639 | A1* | 5/2008 | Pettitt | G01J 3/46 345/589 |
| 2011/0317149 | A1* | 12/2011 | Shimbo | G01J 3/462 356/72 |
| 2013/0182256 | A1* | 7/2013 | Kubota | G01J 3/42 356/402 |

OTHER PUBLICATIONS

Xiandou Zhang, et al., Estimating Spectral Reflectance from Camera Responses Based on CIE XYZ Tristimulus Values Under Multi-Illuminants, Color research and application, Feb. 2017, pp. 68-77, vol. 42, No. 1.

* cited by examiner

*Primary Examiner* — Shawn Decenzo
(74) *Attorney, Agent, or Firm* — Leason Ellis LLP

(57) ABSTRACT

A method and a system are provided to measure transmittance or reflectance of a color specimen by using a transformation matrix obtained from the measurement values of a series of known transmittance or reflectance calibration color standards and multiple flashes from different illumination sources. A color spectrum can be determined with reduced error by calculating the reflectance spectra of an object using measurement matrices obtained under at least two illuminants and the transformation matrix.

19 Claims, 8 Drawing Sheets

SPECTRUM RECOVERY IN A SAMPLE

FIELD OF THE INVENTION

The present invention is directed to apparatus, systems and methods for identifying the transmissive or reflective properties of a sample.

BACKGROUND OF THE INVENTION

There is often a need to determine the transmissive or reflective properties of an object. The color of a sample can be determined by measuring its transmittance or reflectance properties at different wavelengths. For example, it is known to measure light that has been reflected from or transmitted through an object at wavelengths from 400 nm to 700 nm, typically at 10 nm intervals. However, to obtain accurate measurements of the spectrum of an object, a color sensor must have sufficient wavelength channels. Sensors with many wavelength channels (typically 31) produce highly accurate measurements but have cost and complexity drawbacks. Conversely, a sensor with few wavelength channels will lose some of the measurement fidelity and produce a less accurate measurement. Specifically, when the number of wavelength channels are limited, the color information obtained will be less accurate.

In cases of low measurement fidelity, a series of known transmittance or reflectance color standards can be measured, and matrix transformation can be usually used to recover the transmittance or reflectance of the specimen. However, using such matrix transformation will always introduce error that yields less than satisfactory results.

For example, commonly owned U.S. Pat. No. 8,532,371, the contents of which are herein incorporated by reference in its entirety, teaches use of an RGB camera in conjunction with three (3) intermittent light sources to generate nine (9) effective channels. The U.S. Pat. No. 8,532,371, describes estimating from three (3) spectral channels of the spatial pixels, a tristimulus values.

However, what is needed in the art is a system, method and apparatus that utilizes more than three (3) spectral channels to determine or estimate spectra values, not tristimulus values.

Thus, what is needed in the art is a system that improves upon and advances the technological field of color identification. For example, what is needed are systems and methods that utilize multiple known illuminants to improve measurement data such that the end results provide a more precise color measurement value for an object under analysis. Furthermore, what is needed in the art are systems and methods to improve the measurement obtained using sensors having few wavelength channels.

What is also needed is a solution to the problem introduced by using matrices to correct for inaccuracy of estimation due to a low number of measurement channels.

SUMMARY OF THE INVENTION

In one or more implementations described herein, an apparatus is provided for obtaining a reflectance or transmittance spectra of a color sample. A light measurement apparatus for measuring the spectra of a sample, in a non-limiting configuration, comprises at least two illuminants, wherein each illuminant is configured to produce a light beam having a different spectral power distribution (SPD), a color measurement device configured to generate an output signal in response to light being incident on a portion thereof. By way of non-limiting example, the color measurement device is configured to output a signal in response to light being incident upon a light or other sensor element integral or associated with the color measurement device. The apparatus further includes a processor, configured to receive the output signal from the color measurement device and calculate a reflectance spectrum of the sample using at least the output signal generated when the sample is illuminated by each illuminant independent of the other illuminant.

In a further implementation, a method is provided that includes capturing, using a color sensing device, a first measurement of a sample under a first illuminant. Using this first measurement, a measurement value is derived. A second measurement of the sample is captured under a second illuminant and a second measurement value is derived. A processor, having a memory and configured to execute code, is configured to calculate a reflectance or transmissive spectrum of the color sample using the first and second measurement values and a transformation value. The processor is further configured, by code executing therein, to output at least the calculated color value.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF CERTAIN EMBODIMENTS OF THE INVENTION

By way of overview and introduction, various embodiments of the apparatus, systems and methods described herein are directed towards color measurement and analysis. The color of a specimen or sample can be determined by measuring its transmittance or reflectance at different wavelengths, for example, from 400 nm to 700 nm at 10 nm intervals. To make such measurements requires using a color measurement device (such as a multi-channel color sensor) with a sufficient number of wavelength channels. However, color sensors having multiple wavelength channels (such as 31 wavelength channels) can be costly. Color sensors that have fewer wavelength channels are more cost efficient, but the resulting color information obtained is generally less accurate. In one implementation of the apparatus, systems and methods provided herein, a series of color standards having known transmittance or reflectance values are measured under at least two (2) illuminants. Using these measurements, a processor is configured by code executing therein to transform the measurements into a transformation matrix. This transformation matrix is used, along with measurements taken of an unknown color sample under at least two (2) illuminants, to generate a reflectance or transmissive spectra of the unknown sample. Such generated spectra are more accurate than those achieved using the measurement obtained by the color sensor alone; the instrument's measurements are equivalent in accuracy to measurements made using a sensor having a greater number of wavelength channels.

Figure 1A:
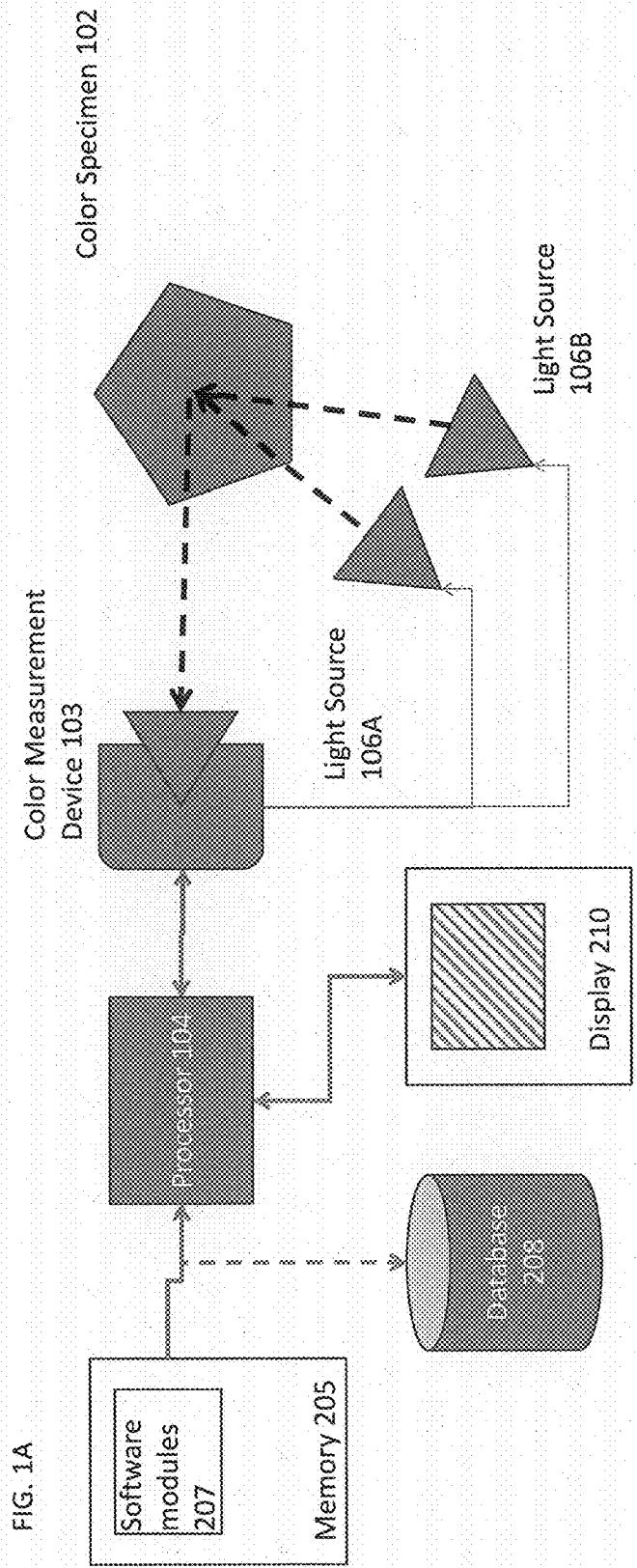
FIG. 1A illustrates a block diagram of a color measurement system according to one embodiment of the present invention.
Figure 1B:
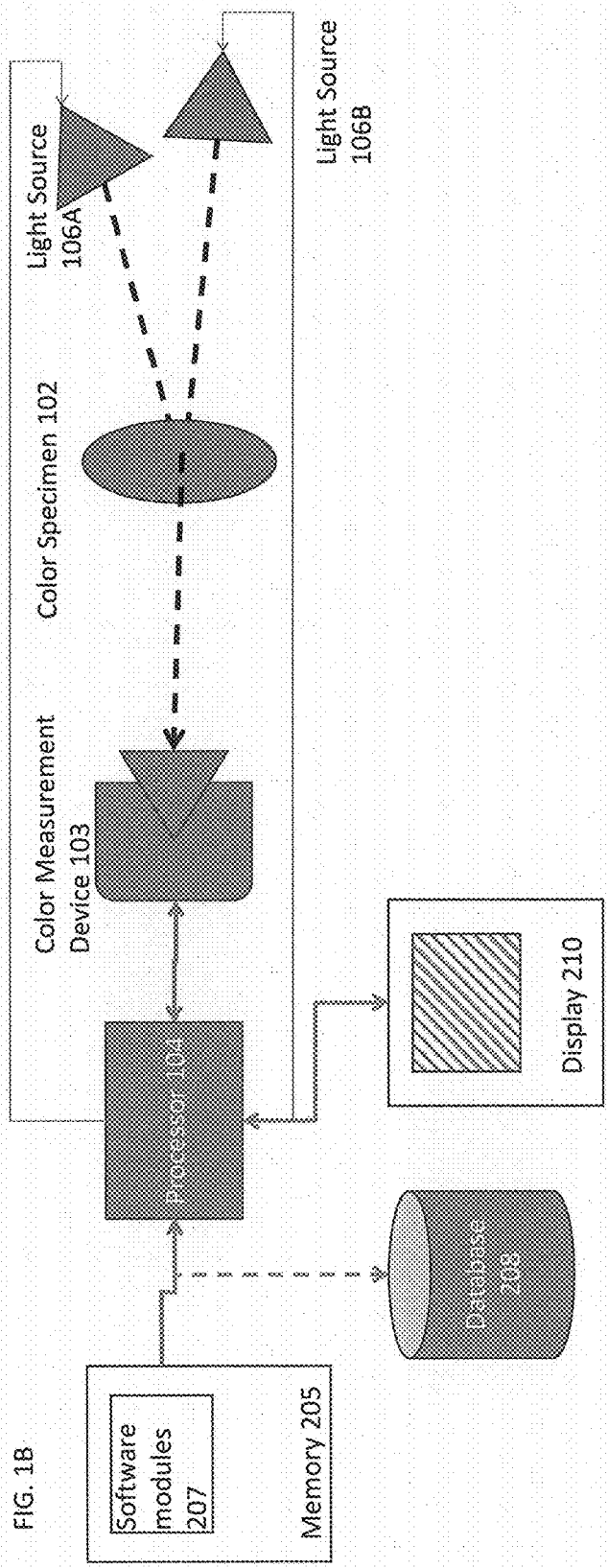
FIG. 1B illustrates a block diagram of a color measurement system according to an alternative embodiment of the present invention.

Turning to FIGS. 1A-B, a color sample 102 is provided for measurement by a color sensor 103. Here, the color sample 102 can be any type or form of physical article having color or spectral properties in need of analysis. In one implementation, the color sample 102 is sample of a material under production having reflective or transmissive properties. For instance, the color sample 102 is a fabric sample such as fleece or fabric blends. In another implementation, the color sample 102 is a sheet of translucent or semi-translucent material. In yet a further implementation, the color sample 102 is an object or item integral to a larger structure or item, such as a dashboard of an automobile, or a section of wall of a structure. For example, the color sample 104 is a section or portion of stucco, carpe, building materials, housing, chassis, packaging, or another item.

With continued reference to FIGS. 1A-B, the color sample 102 is placed such that the sample 102 can be illuminated by at least two (2) different illuminants. In one or more implementations, the illuminants 206A and 206B are commercially available lighting sources. For instance, the illuminants 106A-B, are separate devices that are configurable to produce a light with certain spectral power distributions. For instance, the light sources 106A-B are one or more discrete light emitting elements, such as LEDs, OLEDs, fluorescent, halogen, xenon, neon, D65 light, fluorescent lamp, mercury lamp, Metal Halide lamp, HPS lamp, incandescent lamp or other commonly known or understood lighting sources.

In one or more implementations, the illuminants 106A-B include a lens, filter, screen, enclosure, or other elements (not shown) that are utilized in combination with the light source of the illuminant 106A-B to direct a beam of illumination, at a given wavelength, to the sample 102.

In one implementation, the illuminant 106A-B are operable or configurable by an internal processor or other control circuit. Alternatively, the illuminant 106A-B are operable or configurable by a remote processor or control device having one or more linkages or connections to the illuminant 106A-B. For example, as shown in FIG. 1B, the processor 104 is connected to the illuminant 106A-B. In an alternative configuration shown in FIG. 1A, the illuminant 106A-B are directly connected to a color measurement device 103.

As shown in FIG. 1A, the illuminant 106A-B are positioned relative to the sample 102 and color measurement device 103 so as to provide a 45/0, d/8, or other illumination/pickup geometry combination. However, as shown in FIG. 1B, where the sample 102 is a transmissive sample, the orientation of the illuminants 106A-B relative to the sample 102 and the color measurement device 103 is such that the light beam is directed though the sample 102 to the color measurement device 103.

Continuing with FIGS. 1A-B, light incident upon the sample 102 is captured or measured by a color measurement device 103. Here, the color sensing device can be a color sensor or image capture device. For example, the color measurement device 103 is a scientific CMOS (Complementary Metal Oxide Semiconductor), CCD (charge coupled device), colorimeter, spectrometer, spectrophotometer, photodiode array, or other light sensing device and associated hardware, firmware and software. In one arrangement, the color measurement device 103 is configured to generate an output signal upon light being incident upon a portion of the color measurement device. By way of non-limiting example, the color measurement device is configured to output a signal in response to light being incident upon a light or other sensor element integral or associated with the color measurement device For instance, the color measurement device 103 is configured to generate a digital or analog signal that corresponds to the wavelength or wavelengths of light that are incident upon a light sensor integral to the color measurement device. In one or more configurations, the color measurement device 103 is configured to output spectral information, RGB information, or other multi-wavelength data representative of light reflected off, or transmitted through, the sample 102.

In one or more implementations, the color measurement device 103 has less than 31 wavelength channels. In a further implementation, the color measurement device 103 has less than 15 wavelength channels. In a non-limiting example, the color measurement device 103 has six (6) wavelength channels.

In one non-limiting implementation, the color measurement device 103 is a camera or image recording device integrated into a smartphone, tablet, cell phone, or other portable computing apparatus. In a further embodiment, the color measurement device 103 is an "off the shelf" digital camera or web-camera connected or in communication with one or more computing devices.

The color measurement device 103, in accordance with one embodiment, is a stand-alone device capable of storing local data corresponding to measurements made of the sample 102 within an integrated or removable memory. In an alternative implementation, the color measurement device 103 is configured to transmit one or more measurements to a remote storage device or processing platform, such as processor 104. In configurations calling for remote storage of image data, the color measurement device 103 is equipped or configured with network interfaces or protocols usable to communicate over a network, such as the internet.

Alternatively, the color measurement device 103 is connected to one or more computers or processors, such as processor 104, using standard interfaces such as USB, FIREWIRE, Wi-Fi, Bluetooth, and other wired or wireless communication technologies suitable for the transmission measurement data.

The output signal generated by the color measurement device 103 is transmitted to one or more processor(s) 104 for evaluation. In one implementation, the processor 104 is located within the same device as the color measurement device 103. However, in another implementation, the processor 104 is remote or separate from the color measurement device 103.

In one configuration, the processor 104 is configured through one or more software modules to generate, calculate, process, output or otherwise manipulate the output signal generated by the color measurement device 103.

In one implementation, the processor 104 is a commercially available computing device. For example, the processor 104 may be a collection of computers, servers, processors, cloud-based computing elements, micro-computing elements, computer-on-chip(s), home entertainment consoles, media players, set-top boxes, prototyping devices or "hobby" computing elements.

Furthermore, the processor 104 can comprise a single processor, multiple discrete processors, a multi-core processor, or other type of processor(s) known to those of skill in the art, depending on the particular embodiment. In a particular example, the processor 104 executes software code on the hardware of a custom or commercially available cellphone, smartphone, notebook, workstation or desktop computer configured to receive data or measurements captured by the color measurement device 103 either directly, or through a communication linkage.

The processor 104 is configured to execute a commercially available or custom operating system, e.g., MICROSOFT WINDOWS, APPLE OSX, UNIX or Linux based operating system in order to carry out instructions or code.

In one or more implementations, the color processor 104 is further configured to access various peripheral devices and network interfaces. For instance, the processor 104 is configured to communicate over the internet with one or more remote servers, computers, peripherals or other hardware using standard or custom communication protocols and settings (e.g., TCP/IP, etc.).

The processor 104 may include one or more memory storage devices (memories). The memory is a persistent or non-persistent storage device (such as an IC memory element) that is operative to store the operating system in addition to one or more software modules. In accordance with one or more embodiments, the memory comprises one or more volatile and non-volatile memories, such as Read Only Memory ("ROM"), Random Access Memory ("RAM"), Electrically Erasable Programmable Read-Only Memory ("EEPROM"), Phase Change Memory ("PCM"), Single In-line Memory ("SIMM"), Dual In-line Memory ("DIMM") or other memory types. Such memories can be fixed or removable, as is known to those of ordinary skill in the art, such as through the use of removable media cards or modules. In one or more embodiments, the memory of the processor 104 provides for the storage of application program and data files. One or more memories provide program code that the processor 104 reads and executes upon receipt of a start, or initiation signal.

The computer memories may also comprise secondary computer memory, such as magnetic or optical disk drives or flash memory, that provide long term storage of data in a manner similar to a persistent memory device. In one or more embodiments, the memory of the processor 104 provides for storage of an application program and data files when needed.

The processor 104 is configured to store data either locally in one or more memory devices. Alternatively, the processor 104 is configured to store data, such as image data or processing results, in a local or remotely accessible database 108. The physical structure of the database 108 may be embodied as solid-state memory (e.g., ROM), hard disk drive systems, RAID, disk arrays, storage area networks ("SAN"), network attached storage ("NAS") and/or any other suitable system for storing computer data. In addition, the database 108 may comprise caches, including database caches and/or web caches. Programmatically, the database 108 may comprise flat-file data store, a relational database, an object-oriented database, a hybrid relational-object database, a key-value data store such as HADOOP or MONGODB, in addition to other systems for the structure and retrieval of data that are well known to those of skill in the art. The database 108 includes the necessary hardware and software to enable the color processor 104 to retrieve and store data within the database 108.

In one implementation, each element provided in FIGS. 1A-B are configured to communicate with one another through one or more direct connections, such as though a common bus. Alternatively, each element is configured to communicate with the others through network connections or interfaces, such as a local area network LAN or data cable connection. In an alternative implementation, the color measurement device 103, processor 104, and database 108 are each connected to a network, such as the internet, and are configured to communicate and exchange data using commonly known and understood communication protocols.

In a particular implementation, the processor 104 is a computer, workstation, thin client or portable computing device such as an Apple iPad/iPhone® or Android® device or other commercially available mobile electronic device configured to receive and output data to or from database 108 and or color measurement device 103. Here, the processor 104 communicates with a display device 110 for displaying data as well as input hardware to permit a user to access information, and to send commands and/or instructions to the processor 104 and the color measurement device. In one or more implementations, the display device 110 is a screen, monitor, display, LED, LCD or OLED panel, augmented or virtual reality interface or an electronic ink-based display device.

Those possessing an ordinary level of skill in the requisite art will appreciate that additional features, such as power supplies, power sources, power management circuitry, control interfaces, relays, interfaces, and/or other elements used to supply power and interconnect electronic components and control activations are appreciated and understood to be incorporated.

Figure 2:
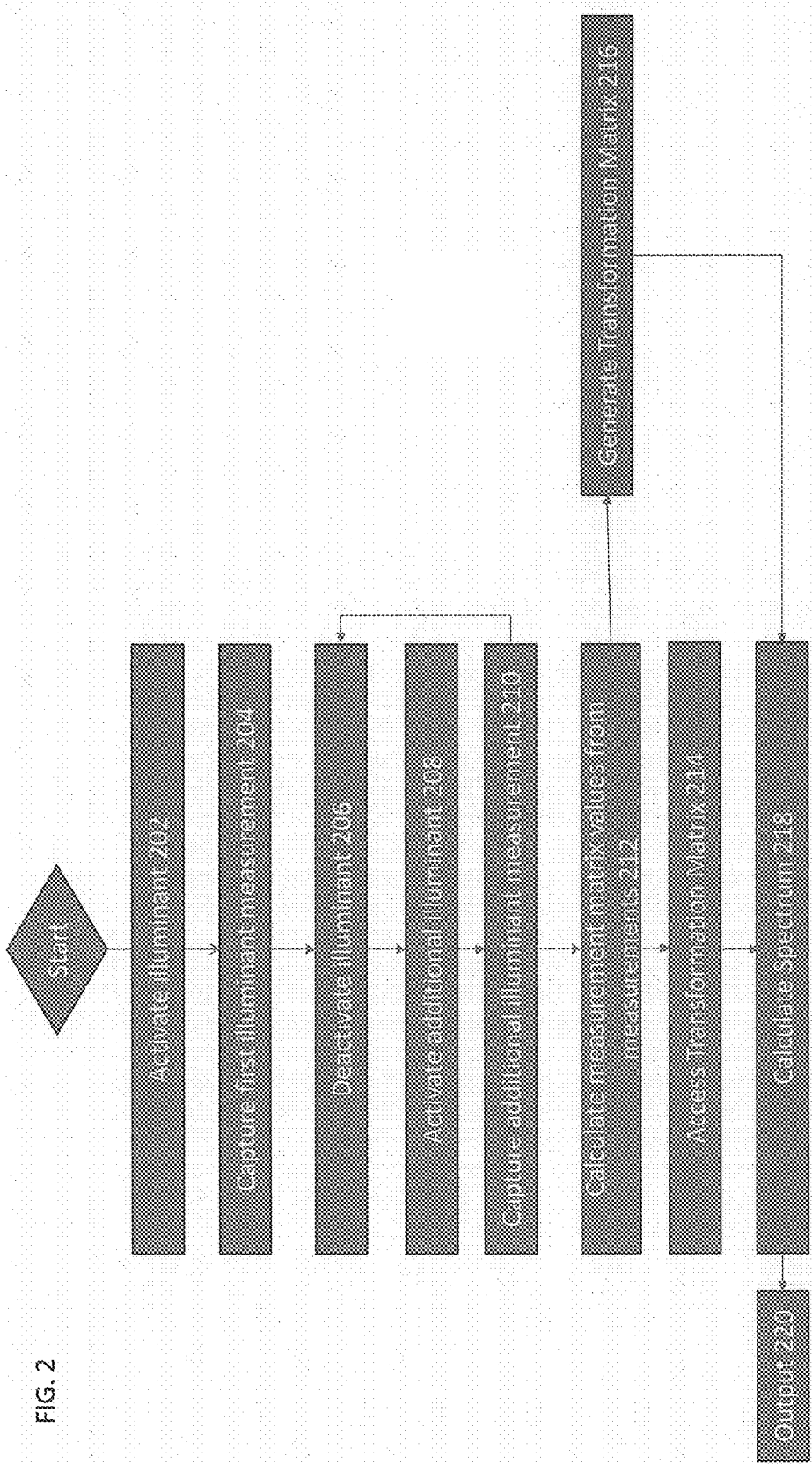
FIG. 2 presents a flow diagram detailing the steps taken in one embodiment of the color measurement system according to one embodiment of the present invention.
Figure 3:
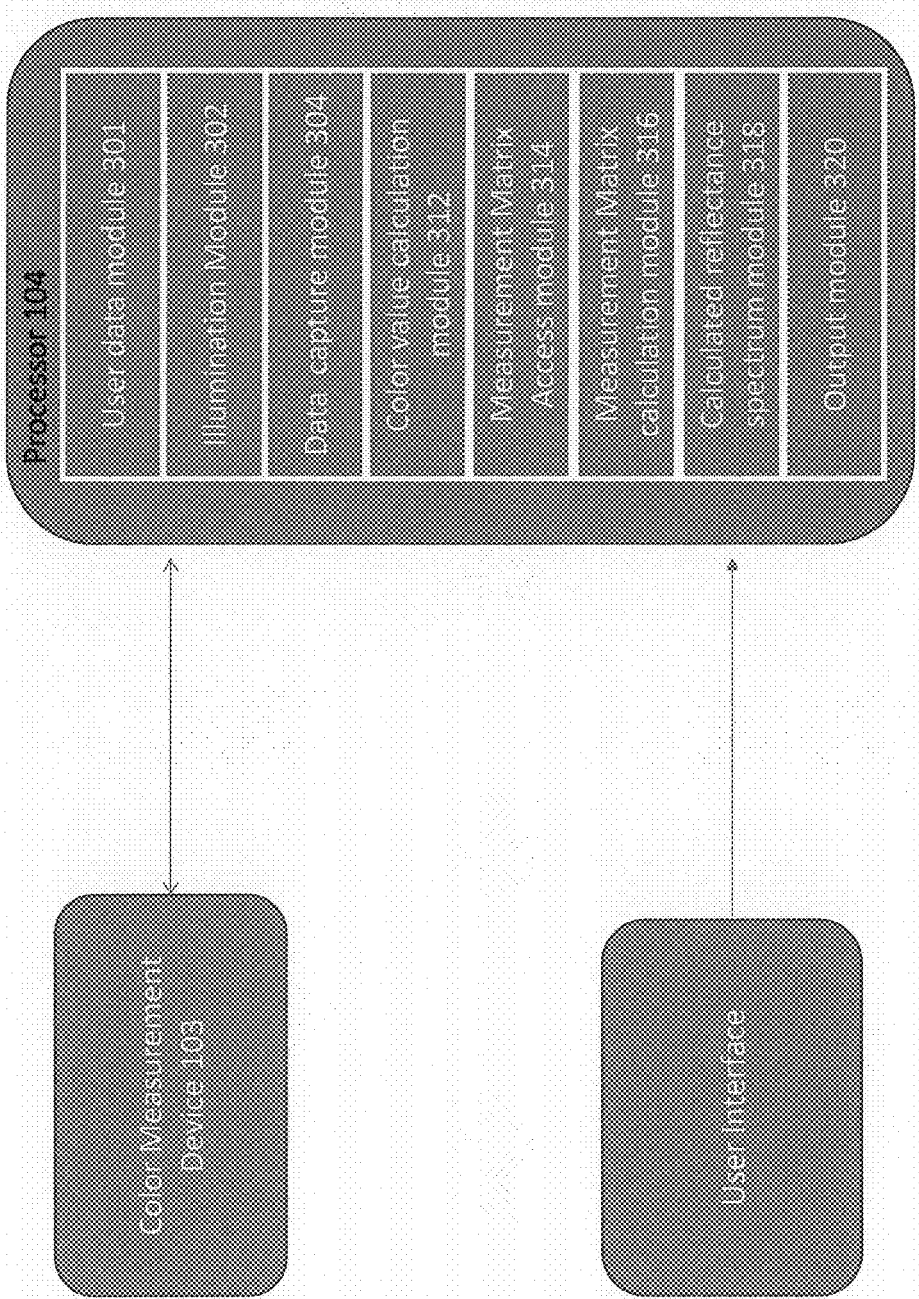
FIG. 3 presents a collection of modules detailing the operative functions of the color measurement system according to one embodiment of the present invention.

Turning to FIGS. 2 and 3, the processor 104 is configured to implement or evaluate the output of the color measurement device 103. With particular reference to FIG. 2, in order to acquire measurements of the sample 102 under at least two illuminants, a color measurement of the sample 102 is made under a first illuminant as shown in step 202. Here, one or more electrical signals causes one of the illuminants 106A-B to activate, thereby sending light of a given SPD to the sample 102. In a particular configuration, one or more illumination modules 302, configured as code executing within the processor 104 configure the processor 104 to activate the desired illuminant. In one or more configurations, the illuminant 106A-B is a broad-band light source, or a light source that includes multiple sub-lighting elements, each capable of emitting a light with a given SPD. Here, one or more submodules of the illuminant module 302 configures the processor 104 to select the desired wavelength or light source available to the illuminant 106A-B.

In one implementation, the illuminant module 302 is configured to select the illuminant based on user input (such as by communicating with the user input module 301) regarding the sample. For example, upon receiving user input regarding the type, nature or category of sample, the processor 104 automatically selects two or more illuminants from the available illuminants to illuminate the sample 102.

Upon illumination by the first illuminant, the light returned from the sample 102 is directed to the color measurement device 103. In response to light incident upon the color measurement device 103, a signal or output is generated that includes information about the sample 102 under analysis. The output or signal is received by the processor 104 as in step 204.

Here, a measurement data capture module 304 configures a processor 104 to capture or record the output of the color measurement device 103. In one implementation, the output captured by the processor 104 configured by a measurement data capture module 304 is composed of a pixel data array, analog signal (or signals), digital data stream, data file, serial encoding, binary data, or other information suitable to contain information about the light that has been incident upon the sample 102 and received by the color measuring device 103.

In a further implementation, one or more submodules of the measurement data capture module 304 configures the processor 104 to convert, format or otherwise condition the data received from the color measurement device 103. For example, a submodule of the measurement data capture module 304 converts the data from a raw binary data to a digital file.

In a particular implementation, the data captured by the color measurement device 103 is stored within a memory of the processor 104. Alternatively, the data relating to the measurements made of the sample 102 under any of the illuminants 106A-B are stored on a remote database 108 for later retrieval or processing. In yet a further implementation, data regarding the specific make, model, brand, and settings of the color measurement device 103 are stored along with the measurement data.

In a further implementation, the characteristics of the illuminant 106A-B are also stored along with the measurement data. For instance, the processor 104 is configured to activate the illuminant 106A-B in order to record measurement data output by the color measurement device 103 and access the properties of the illuminant 106A-B used. One or more submodules of the data capture module 304 configure the processor 104 to access data regarding the activated illuminant from a look up table or database of illuminants 106A-B. Through one or more additional submodules of the data capture module 304, the processor 104 is configured to associate the characteristics of the specified illuminant 106A-B with the relevant measurement data.

As shown in step 206, the processor 104 is configured by one or more submodules of the illumination module 302 to deactivate the first illuminant. The processor 104 is also configured by one or more submodules of the illumination module 302 to activate an additional illuminant as shown in step 208. Here, the processor 104 is configured by one or more modules cooperating with one another to determine the appropriate or desired illuminant 106A-B. For example, the user input stored or accessible by the user data module 301, configures the processor 104 to select a given illuminant 106A-B based on the type of material under analysis.

Once the first measurements under the first illuminant have been made and the illuminant is deactivated, a second illuminant is activated as in step 208. For instance, upon receiving a ready or available flag from the color measurement device, the processor 104 is configured by the illuminant module 302 (or a submodule thereof) to activate the second illuminant as shown in step 208.

The processor 104 is configured to receive the output of the color measurement device 103 generated upon light that has been incident upon the sample 102. Upon illumination of the sample 102 under the second illuminant, the processor 104 is configured by the data capture module 304 to obtain the output of the color measurement device 103 using the second illuminant, as shown in step 210.

In one or more particular implementations, further illuminants are used to capture additional data relating to the sample 102 under different wavelengths. In this arrangement, the processor 104 is configured to return to step 206 and proceed to step 210. For instance, where the user data module 301 configures the processor 104 to capture measurement data under each illuminant 106A-B available to the system or apparatus so described, the processor 104 iterates through steps 206-210 until each illuminant 106A-B has illuminated the sample 102 and corresponding data has been captured and/or stored in the local or remote memory 205.

Using the measurement data obtained under each illuminant, the color (e.g. reflectance or transmittance) values of the sample 102 are calculated as shown in step 212. For example, the processor 104 is configured by a color value calculation module 312 to access the stored values relating to the measurements obtained under the different illuminants. The stored values are used to calculate a measurement matrix for each illuminant. In turn, these light source dependent measurement matrices are used to generate a reflectance response that provides a greater level of accuracy than can be obtained simply using the raw direct measurements obtained by color measurement device with only a few spectral channels.

In one non-limiting implementation, the processor 104 is configured by the measurement matrix calculation module 312, or a submodule thereof, to calculate measurement matrices from the output of the color measurement device 103 under different illuminants.

In one or more implementations, the measurement matrices are calculated by the processor 104 configured by the color value calculation module 312 according to:

$$W_1(t,n) = R(t,\lambda) * \text{diag}(P_1(\lambda)) * S(\lambda,n) \qquad (1)$$

$$W_2(t,n) = R(t,\lambda) * \text{diag}(P_2(\lambda)) * S(\lambda,n) \qquad (2)$$

Here, $S(\lambda, n)$ corresponds to the response matrix of the color measurement device 103 in response to light incident upon it. Furthermore $n=1, 2, \ldots, N$ and corresponds to the number of color channels present in the color measurement device 103 while $\lambda$ is the wavelength of the light incident upon the color measurement device 103. Furthermore, $R(t, \lambda)$ is the reflectance of standard t and wavelength $\lambda$, where $t=1, 2, \ldots T$ and corresponds to the total number of standards. Furthermore, $P_1(\lambda)$ and $P_2(\lambda)$ corresponds to the first and second illuminants respectively.

In a further implementation, additional measurement matrix generated from additional illuminants (e.g. $3^{rd}$, $4^{th}$, ... $N^{th}$) are incorporated into the calculation.

Using a transformation matrix, M, with the calculated measurement values $W_1$ and $W_2$ results in an improved reflectance spectrum of sample 102 relative to a direct measurement of the sample with the color measurement device 103.

In one particular implementation, M is accessed or retrieved from a local or remote data storage device or database 108 as shown in step 214. In an alternative configuration the value for M is derived or calculated based on calibration or standards measurements as shown in step 216. For example, M is calculated using one or more measurements of known reflectance standard(s) under the first and second illuminant. The obtained measurements are used to calculate measurement matrices for the known color standards under the first and second illuminants. Since the reflectance value of the known standards is also known, the processor 104 is configured by a measurement matrix calculation module 316 to generate the transformation matrix M. In one non-limiting implementation, the processor 104 is configured to generate a transformation matrix M using pseudo-inverse calculation such that:

$$M = \text{pinv}([W_1, W_2]) * R \quad (3)$$

Here, $W_1$ and $W_2$ are measurement matrices of calculated from the output of the color measurement device 103 when known color value samples are illuminated under at least a first and second illuminant (using calculation 1 and 2 respectively). Those skilled in the art will appreciate that the M matrix value obtained according to calculation (3) provides a more accurate measurement of the color values of the sample compared to a traditional matrix obtained using only a single illumination source.

Independent of the source of M, once obtained, the value $R_{calculated}$ is obtained according to:

$$R_{calculated} = [W_1, W_2] * M \quad (4)$$

Using transformation matrix M, a reflectance spectrum for an unknown color sample measured under illuminant $P_1$ and $P_2$ can be derived, as shown in step 218. Here, $W_1, W_2$ represent the measurement matrices of the unknown sample under illuminant $P_1$ and $P_2$. This derived spectrum is more accurate than what is typically available with a low wavelength channel color measurement device. For instance, using the measurement matrices calculated in step 312, the processor 104, configured by a calculated reflectance spectrum module 318, calculates a reflectance spectrum for the sample 102 utilizing the transformation matrix M derived according to calculation 3 or accessed from a database or storage device.

Once the reflectance spectrum has been generated, the processor 104 is configured by an output module 320 to store the generated reflectance spectrum to a local or remote database, and/or to generate on a display 110 the reflectance spectrum, as in step 220.

As noted, the present systems, methods and apparatus, described herein provide an improvement over the art of color measurement. According to the features and disclosures provided, a color sensor, when used in combination with multiple light sources, can achieve a measurement result that improves upon the results achievable with a measurement device having a limited the number of wavelength channels. As a result, more improved measurements are obtainable using less expensive or complex sensor platforms. For example, FIG. 4 provides a simulated color measurement that demonstrates how the multiple illuminants can improve the recovery of reflectance spectrum of a sample 102.

Figure 4:
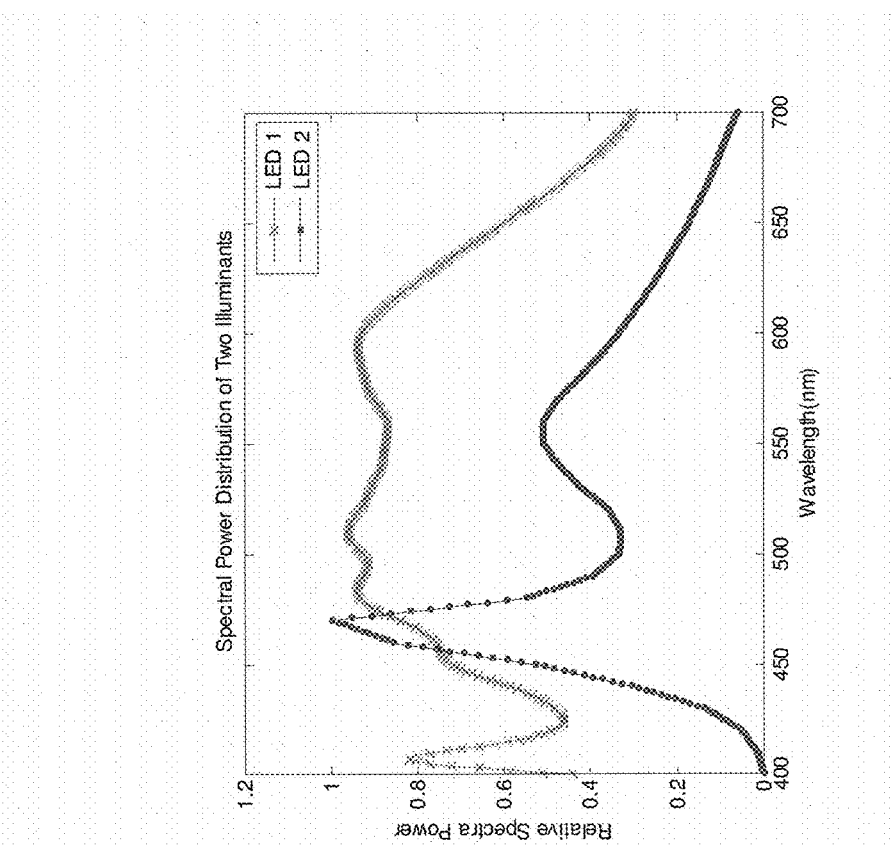
FIG. 4 is a chart detailing the spectral power distribution of two illuminants in accordance with one aspect of the present invention.
Figure 5:
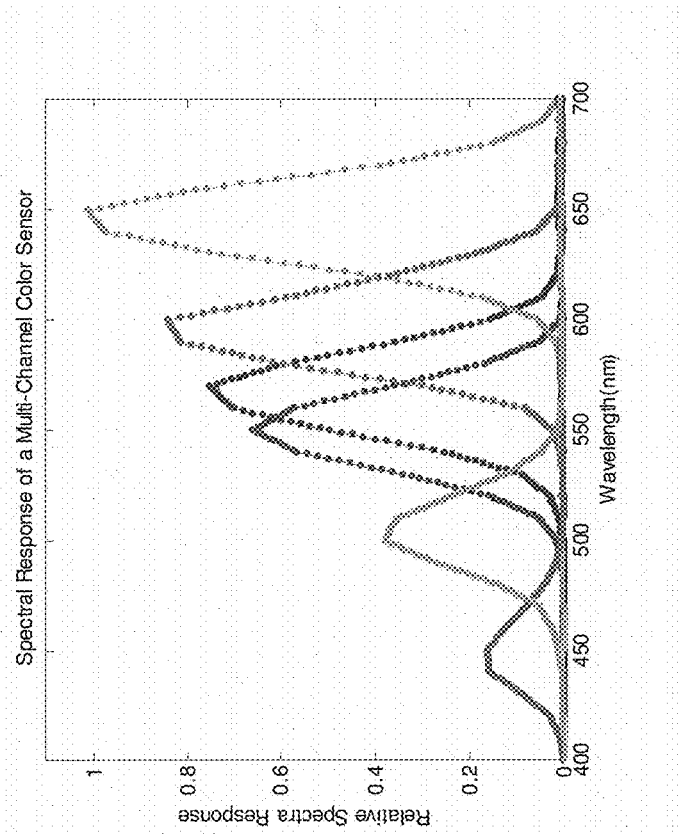
FIG. 5 is a chart detailing the spectral response of a multi-channel color sensor in accordance with one aspect of the present invention.
Figure 6:
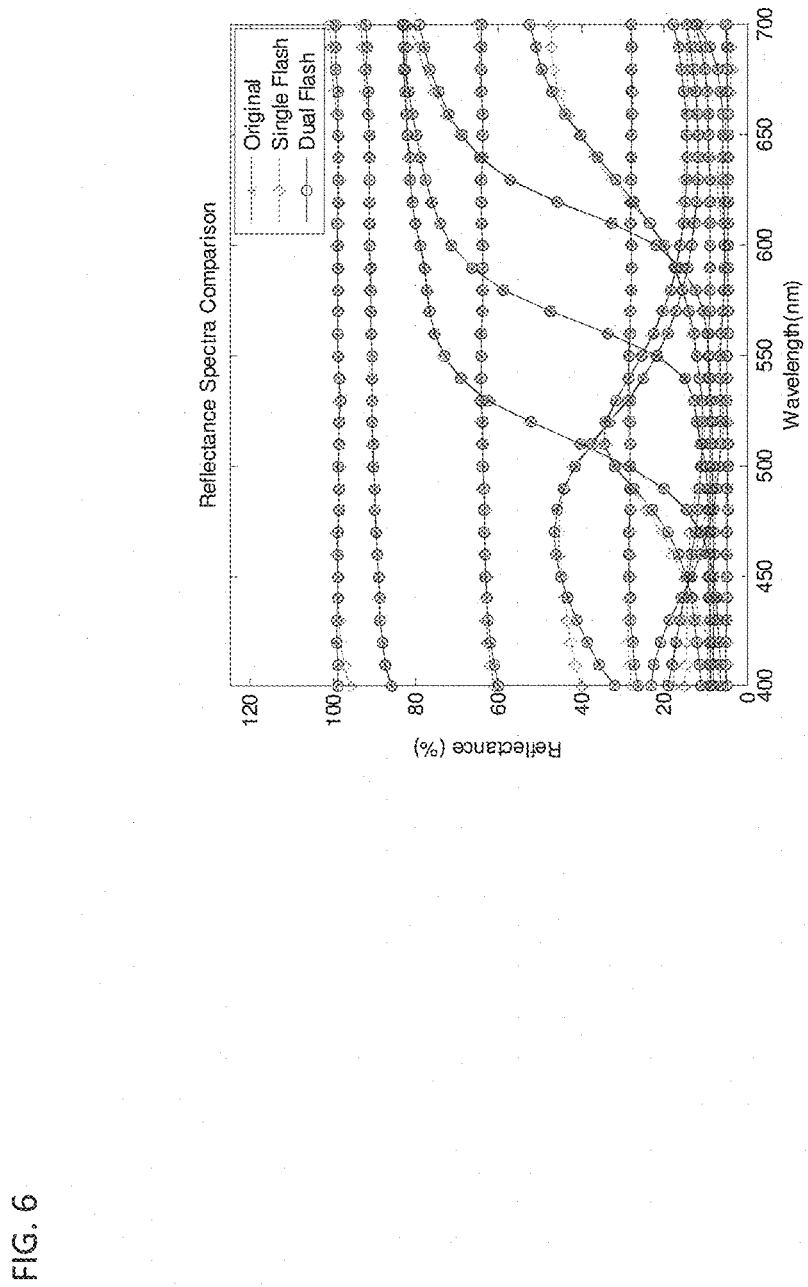
FIG. 6 is a chart comparing reflectance spectra according to one embodiment of the present invention.

In the example of FIG. 4, two LED light sources having wavelength outputs specified by the x-axis were used. The relative spectral power distribution (SPD) of the two LEDs are provided on the y-axis. Likewise, FIG. 5 provides the spectral response of a 6-channel color sensor. Here, the y-axis denotes the relative spectral response and the x-axis denotes the wavelength. From equations (1) and (2), the color sensor response $W_1$ and $W_2$ using two different LEDs can be calculated in order to simulate the measurement result of the sensor. Since the reflectance standards are known (provided in FIG. 6), the transformation matrix value M can be calculated from equation (3). Using these inputs, a processor can be suitably configured to recover the reflectance spectra of a sample 102. As shown, FIG. 6 provides the calculated reflectance using single illuminant LED1 and dual illuminants LED1 and LED2, compared to the original known reflectance of the calibration standards. Furthermore FIG. 7 shows the color difference of dE CIELAB between the original reflectance and the spectrum obtained using a single flash (using only one LED) or dual-flash (using two LEDs in sequence).

Figure 7:
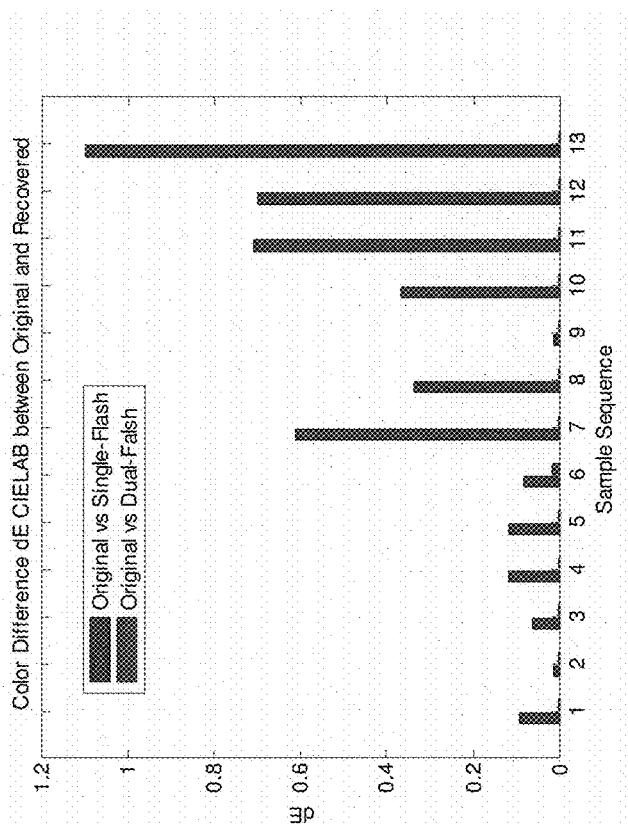
FIG. 7 is a chart comparing the color difference between measurement data and actual color values in accordance with one aspect of the present invention.

Both FIGS. 6 and 7 demonstrate that the reflectance spectrum obtained by measurements using at least two illuminants is closer to the actual spectrum of the calibration objects. It should be appreciated two or more illuminants, with different SPDs, and their combinations can be used to further reduce the error of matrix transformation and provide a more accurate measurement of the color of a sample.

While this specification contains many specific embodiment details, these should not be construed as limitations on the scope of any embodiment or of what can be claimed, but rather as descriptions of features that can be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems cited throughout this application are incorporated by reference herein. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those claims, and by equivalents of such features.

What is claimed is:

1. A light measurement apparatus for measuring the spectrum of a sample, the light measurement device comprising:
    at least two broadband illuminants, wherein each illuminant is configured to produce a light beam having a different spectral power distribution (SPD),
    a color measurement device configured to generate an output signal in response to light being incident on at least one portion of the color measurement device, and
    a processor, configured to receive the output signal from the color measurement device and calculate a reflectance spectrum of the sample using at least each output signal generated when the sample is illuminated by each illuminant independent of any other illuminant.

2. The apparatus of claim 1, wherein the color measurement device has fewer than 31 spectral channels.

3. The light measurement apparatus of claim 1, further comprising a display device to display the calculated reflectance spectrum of the sample.

4. A method for identifying the color properties of a sample, the method comprising:
    capturing, using a color sensing device, a first measurement of a sample under analysis under a first broadband illuminant;
    deriving, using at least one processor, a first measurement value from the first measurement of the sample;
    capturing, using the color sensing device, at least a second measurement of the sample under at least a second broadband illuminant;
    deriving, using at least one processor, at least a second measurement value from the at least a second measurement sample;
    generating, using at least one processor having memory and configured to execute code, a calculated color value for the sample using at least the first and second measurement values and a transformation value; and
    outputting at least the calculated color value.

5. The method of claim 4, wherein the calculated color properties comprise a reflectance spectrum.

6. The method of claim 5, wherein the calculated color properties are calculated according to:

$$R_{calculated} = [W_1, W_2] * M$$

where $W_1$ and $W_2$ are measurement matrices of the sample obtained under the first and second illuminant and M is a transformation matrix.

7. The method of claim 4, wherein the calculated color value is a transmittance spectrum.

8. The method of claim 4, wherein the generating step further includes the step of accessing from a memory, the transformation value.

9. The method of claim 8, wherein the memory is remote from the at least one processor.

10. The method of claim 4, wherein the generating step further generating the transformation value by:
    obtaining color measurements of one or more color reference objects under at least two illuminants, where each of the one or more color reference objects has a known reflectance value for each of a set of wavelengths;
    deriving, using at least one processor, a first measurement value from the one or more measurements made under the first illuminant;
    deriving, using at least one processor, a second measurement value from the one or more measurements made under the second illuminant;
    generating the transformation value using at least the first measurement value under the first illuminant the second measurement value under the second illuminant, and the known reflectance values.

11. The method of claim 10, wherein the transformation value is expressed as a matrix.

12. The method of claim 11, wherein the transformation matrix is calculated using a matrix pseudoinverse of the measurement matrix.

13. The method of claim 12, wherein the transformation matrix is calculated using a Moore-Penrose pseudo-inverse.

14. The method of claim 13, wherein the transformation matrix M is calculated according to:

$$M = \text{pinv}([W_1, W_2]) * R$$

where, $W_1$, $W_2$, are the respective measurement matrices under the first illuminant and second illuminant, and R is the reflectance value of the known color reference object.

15. The method of claim 4, wherein the first and second measurement values are measurement matrices calculated according to:

$$W(t,n) = R(t,\lambda) * \text{diag}(P(\lambda)) * S(\lambda,n)$$

where wavelength $\lambda$ is the wavelength of the illuminant P used to illuminate the sample, the color measurement device response value is $S(\lambda, n)$, where n=r, g, or b, and the reflectance standard of the sample is provided by $R(t, \lambda)$, where t=1, 2, ... T and T is the total number of reflectance standards.

16. The method of claim 4, where the step of obtaining a known illuminant measurement value includes:
    accessing from a data storage location, a plurality of known reflectance spectra for different colors obtained under a plurality of illuminants; and calculating a measurement matrix using the reflectance spectra.

17. The method of claim 4, wherein the measurement values are expressed as a matrix.

18. The method of claim 4, further comprising:
    capturing, using the color sensing device, at least a third measurement of the sample under at least a third illuminant;

deriving, using at least one processor, at least a third measurement value from the at least the third measurement of the sample.

19. A system for identifying the color of a sample, the system comprising:
at least two broadband illuminants, wherein each illuminant is configured to produce a light beam having a different SPD,
   a color measurement device configured to generate an output signal in response to light being incident on at least a portion of the color measurement device, and
a processor, having a memory and configured to:
   receive from the color measurement device, a first measurement of a sample under analysis under at a first illuminant;
   derive a first measurement value from the first measurement of the sample;
   capture at least a second measurement of the sample under at least a second illuminant;
   receive from the color measurement device at least a second measurement value from the at least a second measurement sample;
   generate a calculated color value for the sample using at least the first and second measurement values and a transformation value; and
   output at least the calculated color value.

* * * * *